United States Patent
Dhanaraj et al.

(10) Patent No.: US 10,980,913 B2
(45) Date of Patent: Apr. 20, 2021

(54) SEALANT FOAM COMPOSITIONS FOR LUNG APPLICATIONS

(71) Applicant: Ethicon LLC, Guaynabo, PR (US)

(72) Inventors: Sridevi N. Dhanaraj, Raritan, NJ (US); Nir I. Nativ, West Orange, NJ (US); Ashley DeAnglis, Skillman, NJ (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/911,859

(22) Filed: Mar. 5, 2018

(65) Prior Publication Data

US 2019/0269818 A1 Sep. 5, 2019

(51) Int. Cl.
| | |
|---|---|
| *A61L 24/00* | (2006.01) |
| *C08J 9/00* | (2006.01) |
| *C08J 9/12* | (2006.01) |
| *A61L 24/04* | (2006.01) |
| *A61L 24/02* | (2006.01) |

(52) U.S. Cl.
CPC ....... *A61L 24/0036* (2013.01); *A61L 24/0042* (2013.01); *A61L 24/02* (2013.01); *A61L 24/043* (2013.01); *C08J 9/0061* (2013.01); *C08J 9/125* (2013.01); *A61L 2400/04* (2013.01); *A61L 2400/06* (2013.01); *C08J 2203/10* (2013.01); *C08J 2207/10* (2013.01); *C08J 2389/00* (2013.01); *C08J 2471/02* (2013.01)

(58) Field of Classification Search
USPC ......................................................... 424/486
See application file for complete search history.

(56) References Cited

U.S. PATENT DOCUMENTS

| | | | |
|---|---|---|---|
| 5,840,777 A | 11/1998 | Eagles et al. | |
| 5,874,500 A | 2/1999 | Rhee et al. | |
| 6,258,351 B1 | 7/2001 | Harris | |
| 6,458,147 B1 | 10/2002 | Cruise et al. | |
| 6,566,406 B1 | 5/2003 | Pathak et al. | |
| 6,730,299 B1 | 5/2004 | Tayot et al. | |
| RE38,827 E | 10/2005 | Barrows et al. | |
| RE39,321 E | 10/2006 | MacPhee et al. | |
| 7,129,210 B2 | 10/2006 | Lowinger et al. | |
| 7,597,882 B2 | 10/2009 | Pathak et al. | |
| 7,766,891 B2 | 8/2010 | McGurk et al. | |
| 8,034,367 B2 | 10/2011 | Hnojewyj | |
| 8,057,818 B2 | 11/2011 | Yuksel et al. | |
| 8,071,124 B2 | 12/2011 | Yuksel et al. | |
| 8,198,365 B2 | 6/2012 | Ingenito et al. | |
| 8,314,211 B2 | 11/2012 | Falus | |
| 8,349,349 B2 | 1/2013 | Sargeant et al. | |
| 8,383,144 B2 | 2/2013 | Hnojewyj | |
| 8,668,899 B2 | 3/2014 | Dowling et al. | |
| 8,680,240 B1 | 3/2014 | Falus et al. | |
| 8,911,750 B2 | 12/2014 | Tsai et al. | |
| 9,168,325 B2 | 10/2015 | Goessl et al. | |
| 9,295,752 B1 | 3/2016 | Girdhar | |
| 2002/0192271 A1 | 12/2002 | Hedner et al. | |
| 2003/0211137 A1 | 11/2003 | Sierra | |
| 2006/0062768 A1 | 3/2006 | Hnojewyj | |
| 2007/0254016 A1 | 11/2007 | Andersen et al. | |
| 2009/0221496 A1 | 9/2009 | Suematsu et al. | |
| 2009/0287313 A1 | 11/2009 | Lowinger et al. | |
| 2010/0227804 A1 | 9/2010 | Sasaki | |
| 2011/0021431 A1 | 1/2011 | Jones et al. | |
| 2011/0104280 A1 | 5/2011 | Hnojewyj | |
| 2011/0293722 A1 | 12/2011 | Kaully | |
| 2013/0116341 A1 | 5/2013 | Askari et al. | |
| 2014/0369991 A1 | 12/2014 | Schutte et al. | |
| 2015/0272883 A1 | 10/2015 | Laub | |
| 2017/0239385 A1* | 8/2017 | Ingenito | C08J 3/075 |

FOREIGN PATENT DOCUMENTS

| | | |
|---|---|---|
| CN | 105521521 A | 4/2016 |
| WO | WO2008065329 A2 | 6/2008 |
| WO | WO 2009/153748 | 12/2009 |

OTHER PUBLICATIONS

Corrales (Biomecánica, vol. 24, 2016, pp. 14-23).*
Clark Fuller, Reduction of intraoperative air leaks with progel in pulmonary resection : a comprehensive review, Journal of Cardiothoracic surgery, Apr. 16, 2013, pp. 1-7, vol. 8 Issue 1, WO.

* cited by examiner

*Primary Examiner* — Devang K Thakor

(74) *Attorney, Agent, or Firm* — David R. Crichton; Leo Kriksunov

(57) ABSTRACT

The present invention is directed to tissue sealant compositions comprising: a multi-arm reactive polyethylene glycol polymer having at least 3 electrophilic groups; albumin; a buffer; water; and entrained gas as bubbles; wherein concentration of albumin in a liquid component of the sealant is within range of 50-200 mg/ml; and wherein concentration of multi-arm PEG in said liquid component of the sealant is within range of 25-100 mg/mL.

10 Claims, 9 Drawing Sheets

SEALANT FOAM COMPOSITIONS FOR LUNG APPLICATIONS

FIELD OF THE INVENTION

The present invention relates generally to agents and materials for promoting tissue sealing and hemostasis, more particularly, to resorbable sealants with improved efficacy, particularly in the form of compressible foams, and to methods for manufacturing such compositions. The present invention is directed to tissue sealant compositions comprising the reaction product of a multi-arm polyakylene oxide core polymer, preferably polyethylene glycol, having at least 3 electrophilic groups, albumin, a buffer, water and entrained gas as bubbles; wherein concentration of albumin in a liquid component of the sealant is within range of 50-200 mg/ml; and wherein concentration of multi-arm polymer in said liquid component of the sealant is within range of 25-100 mg/mL.

BACKGROUND

Surgeons use tissue sealants in a wide range of different clinical applications. Sealants can be used as both a primary and/or secondary method of joining or sealing tissue. A common class of tissue adhesives is fibrin-based and contains a concentrate of fibrinogen and thrombin. Fibrin adhesives are typically two-component adhesives that when mixed together react to simulate the last stages of the coagulation cascade. The resulting clot adheres to tissue and bridges a gap between the tissues until healing can occur. Glues based on albumin or gelatin cross-linked with an aldehyde are also known. Representative of this class of glues are gelatin-resorcinol cross-linked with formaldehyde or glutaraldehyde. Gelatin-based glues have been extensively studied and shown to generally be effective. Cyanoacrylates, polyurethanes, polymethylmethacrylates, among other synthetic polymers, have been also investigated as tissue glues.

The tissue adhesives/sealants described above are typically delivered as liquids that react and crosslink to form hydrogels. The handling properties of liquids can be a challenge since they get diluted and also are difficult to retain in the area of application. Liquids can also be difficult to visualize at the site of application, especially if they are clear liquids.

Various technologies have been developed for the formulation of tissue adhesives. Some of them are of synthetic origin, such as the glues based on cyanoacrylates (2-butyl cyanoacrylate, 2-octyl cyanoacrylate), or on synthetic polymers (polyurethanes, polymethylmethacrylates) and others contain biological materials such as collagen or fibrin which, in addition, have hemostatic properties and also act by controlling bleeding. As a result of their hemostatic and adhesive properties, sealants, and particularly fibrin sealants-have been extensively used in most surgical specialties for over two decades to reduce blood loss and post-operative bleeding because of the ability to adhere to human tissue as it polymerizes. In some applications, the amount of adhesion to tissue can be sub-optimal with fibrin sealants, and a greater adhesion to the tissue compared with fibrin sealant formulations is needed.

The properties of existing tissue sealants also make it difficult to ensure adequate coverage of the lung, particularly when a minimally invasive technique is used. Adequate coverage of the lung can be important to achieve the thickness and coverage of sealant desired to seal leaks, because leaks can develop at the staple line, adjacent to the staple line, and in the lobes of the lung due to manipulation during the procedure. Due to the minimally invasive approach, current sealants must be applied to a deflated lung. Current sealants may not have the physical properties that allow them to maintain coverage over the entire surface of the lung during and after insufflation.

U.S. Pat. No. 6,458,147 titled Compositions, systems, and methods for arresting or controlling bleeding or fluid leakage in body tissue, discloses a biocompatible and biodegradable material applied to arrest the flow of blood or to seal tissue comprising a mixture of a protein solution comprising recombinant or natural human serum albumin at a concentration of about 25% or less and a polymer solution including a derivative of a hydrophilic polymer with a functionality of at least three, wherein, upon mixing, the protein solution and the polymer solution cross-link to form a mechanical non-liquid covering structure without of a photo-initiator and ultraviolet light energy.

U.S. Pat. No. 7,129,210 titled Tissue adhesive sealant, discloses a tissue adhesive kit consisting: a cross-linkable albumin protein consisting of albumin dissolved or suspended directly in aqueous solvent to form a protein solution; and a cross-linking agent solution comprising an aldehyde and an amino acid containing species reactive with said aldehyde, said aldehyde and said amino acid containing species being present in a ratio between 20:1 and 1:1 applied with said protein solution to form a tissue adhesive sealant.

U.S. Pat. No. 9,168,325 titled Hemostatic foam, discloses a method for preparing a transient pharmaceutical hemostatic liquid foam, the method comprising: providing a pharmaceutical hemostatic liquid foam base preparation comprising albumin and thrombin, wherein: albumin is present in its native form, albumin is not crosslinked, and thrombin is present in a concentration of 100 to 10000 IU/ml; and contacting the pharmaceutical hemostatic liquid foam base preparation with a foaming gas so as to obtain the transient pharmaceutical hemostatic liquid foam.

U.S. Pat. No. 9,295,752 titled Bioadhesive for occluding vessels, discloses a method of occluding a vessel of a mammal, the method comprising: injecting a bioadhesive into a vessel of a mammal to displace blood in the vessel and prevent blood flow back into the vessel and to crosslink the bioadhesive in the vessel to form an occlusion in the vessel, wherein the bioadhesive comprises: (i) a biopolymer having one or more first chemically reactive amine groups; (ii) a biocompatible crosslinker having at least two second chemically reactive groups that can chemically react with the one or more first chemically reactive amine groups of the biopolymer; and (iii) a biocompatible rheological modifier, and wherein the biopolymer and crosslinker form a cross-linked network and the biocompatible rheological modifier does not substantially react with the biopolymer or the biocompatible crosslinker.

U.S. Patent Publication No. 2015/0272883 titled Methods and Compositions for Administering an Active Agent to the Pleura of a Patient, discloses a composition for treating a pleura of a patient, the composition comprising: a liquid component comprising a biocompatible composition having a viscosity which increases in response to an increase in temperature; and an active agent dissolved, dispersed, or suspended in the liquid component, the active agent being capable of causing inflammation and/or adhesion of the pleura.

U.S. Pat. No. 8,680,240 titled Tissue sealant for use in non-compressible hemorrhage, discloses a hemostatic composition containing four solutions comprising the ingredients described in portions a)-d), for cessation of blood loss from injured tissue of a patient's body without application of a compressive force: a) Teleostean (fish) gelatin type A mixed with sucrose, polyvinylpyrrolidone, a water-soluble foam inducer of sodium bicarbonate and dihydrogen phosphate, and human serum albumin in a buffer solution at a pH of about 8.3 in the presence of metallic ions and a gel enhancer selected from the group consisting of alpha-galactosidase degraded carrageenan, alginate sulfate, hyaluronic salt, or hyaluronic acid; B) polyacrylic acid crosslinked with allyl ethers of sucrose (Carbomer homopolymer) containing not less than 56.0 percent and not more than 68.0 percent of carboxylic acid; with a viscosity of a neutralized 0.5 percent aqueous dispersion between 30,500 and 39,400 centipoises; c) fibrin monomer in an acidic solution with a pH 3.4 to pH 4.0 that polymerizes upon change in pH from acid to neutral (7.0-7.2); and d) calcium independent transglutaminase enzyme and calcium chloride in HEPES buffer for stabilizing the fibrin polymer.

U.S. Patent Publication No. 2014/0369991 titled Formulations for Wound Therapy, discloses a pharmaceutical composition comprising an absorbable carrier of a biocompatible, biodegradable polymer and dispersed, at least partially through or on said absorbable carrier, microparticles comprising fibrinogen in an amount of from about 0.1-15 mg/cm$^2$ and/or microparticles comprising thrombin in an amount of from about 0.01 to 500 IU/cm$^2$, wherein the microparticles further comprise a glassy carrier.

U.S. Patent Publication No. 2013/0116341 titled IN-VIVO GELLING PHARMACEUTICAL PRE-FORMULATION, discloses an in vivo gelling pharmaceutical pre-formulation, comprising: (a) at least one water soluble first compound comprising more than one nucleophilic group selected from a thiol and an amino, wherein the first compound is a glycol, trimethylolpropane, pentaerythritol, hexaglycerol, or tripentaerythritol derivative, and wherein the first compound further comprises one or more polyethylene glycol sections; (b) at least one water soluble second compound comprising more than one electrophilic group selected from an epoxide, N-succinimidyl succinate, N-succinimidyl glutarate, N-succinimidyl succinamide or N-succinimidyl glutaramide, wherein the second compound is a trimethylolpropane, glycerol, diglycerol, pentaerythritol, sorbitol, hexaglycerol, tripentaerythritol, or polyglycerol derivative, and wherein the second compound further comprises one or more polyethylene glycol sections; (c) an aqueous buffer in the pH range of 5.0 to 9.0; and (d) optionally, one or more therapeutic agents; wherein mixing the first compound, the second compound, and the optional therapeutic agent in the aqueous buffer and delivering the mixture to a target site in the human body generates the in vivo gelling pharmaceutical pre-formulation such that the in vivo gelling pharmaceutical pre-formulation at least in part polymerizes and gels at the target site to form a biocompatible hydrogel polymer.

U.S. Patent Publication No. 2011/0104280 Wound treatment systems, devices, and methods using biocompatible synthetic hydrogel compositions, discloses a system for promoting wound healing comprising a first solution comprising a biocompatible, synthetic, electrophilic polymer component including a multi-arm poly(ethylene glycol) succinimidyl glutarate (PEG-SG), a second solution comprising a biocompatible, synthetic, nucleophilic polymer component essentially free of human or bovine albumin and other biological molecules and including a polypeptide moiety having a number of active surface lysines of at least twenty (20) per 5000 M/W, and optionally blended with a multi-arm poly(ethylene glycol) amine (PEG-NH), and instructions for use comprising mixing the first and second solutions to form a synthetic hydrogel composition, and applying the synthetic hydrogel composition by topically spraying the synthetic hydrogel composition onto a targeted wound site to promote wound healing.

U.S. Pat. No. 8,314,211 titled Tissue sealant for use in non-compressible hemorrhage discloses a method of sealing injured tissue of a patient's body that utilizes a four-part hemostatic composition including a hydrogel carrier and a fibrin monomer, in combination, for cessation of blood loss from the injured tissue without application of a compressive force independently therefrom, the method comprising the steps of: (a) mixing in a mixing device the following components so as to create a foam: (i) a first component (Part A), in a liquid form, of Teleostean (fish) gelatin type A mixed with sucrose, polyvinylpyrrolidone, and Bovine serum albumin in a selected buffer solution at a pH of about 8.3 in the presence of metallic ions; (ii) a second component (Part B) of a selected, relatively high molecular weight acrylic acid of carbomer and divalent ions in a solution at a pH of about 3.4; (iii) a third component (Part C) of a fibrin monomer in a selected acidic solution that polymerizes upon change in pH; and (iv) a fourth component (Part D) having a selected calcium independent transglutaminase enzyme and calcium chloride for stabilizing the fibrin polymer; and (b) delivering the foam through an outlet of the mixing device to a surgical site of a body cavity, organ or tissue so as to place the foam in contact with the site such that the non-dynamic, non-crosslinked fibrin monomer of the foam sticks to wet tissue of the site and forms a matrix in the patient's blood; wherein the mixing of Parts A, B, C, and D renders the non-crosslinked fibrin monomer dynamic by neutralizing the pH of the overall mixture such that the non-crosslinked fibrin is converted to a fibrin sealant, thereby inducing coagulation of the blood and adhesive properties of severed tissue.

U.S. Patent Publication No. 2011/0021431 titled Methods and Compositions For Medical Articles Produced From Proteinaceous Compounds, discloses a foam composition useful as a tissue sealant, tissue dressing or tissue barrier comprising: (a) an amino acid containing compound selected from the group of albumin, gelatin, collagen, and any combination thereof, and (b) an augmentative polymer selected from the group of chitosan, glucosamine, N-acetyl glucosamine, and any combination thereof.

U.S. Pat. No. 8,911,750 titled Lung volume reduction therapy using crosslinked biopolymers, discloses a method for reducing lung volume in a patient, comprising the steps of a) inserting a bronchoscope through the trachea of a patient in need thereof to reach a lung segment to be treated; wherein said bronchoscope comprises a working channel; b) inserting a catheter through said working channel; and c) administering through the catheter to the lung segment a therapeutically effective amount of a composition comprising a biopolymer, a cross-linker, and a polymeric additive; wherein said polymeric additive accelerates a cross-linking reaction between the biopolymer and the cross-linker; the composition is administered in an amount sufficient to reduce lung volume, but without systemic toxicity; and i) the biopolymer is bovine serum albumin in about 25% by weight of the composition; the cross-linker is glutaraldehyde in about 0.25% by weight of the composition; and the polymeric additive is poly(vinylpyrrolidone) in about 10% by weight of the composition; or ii) the biopolymer is human serum albumin in about 22.5% by weight of the composition; the cross-linker is glutaraldehyde in about 0.3% by weight of the composition; and the polymeric additive is poly(vinylpyrrolidone) in about 4.5% by weight of the composition.

U.S. Patent Publication No. 2007/0254016 titled Biodegradable foam, discloses a method for forming a dried absorbent foam having an open pore network and pores by: a. forming a wet foam from an aqueous dispersion comprising a polysaccharide; a foaming agent; optionally a plasticizer; optionally a crosslinking agent; optionally gel-forming ions; optionally one or more additives, and water; b. mixing a foam from the aqueous dispersion, optionally by mechanical agitation; c. molding or shaping the wet foam and optionally forming a crosslinked foam; and d. drying the foam to form a dried foam optionally by air drying and optionally further molding, shaping or compressing the dried foam.

U.S. Pat. No. 8,349,349 titled Tissue adhesives and sealants and method for their use, discloses a biocompatible composition comprising: an implant comprising a substrate; a first component comprising a biodegradable material including a tissue binding end group and a functional group selected from the group consisting of biotin and avidin; and a second component comprising a biodegradable material including a substrate binding end group and a functional group selected from the group consisting of biotin and avidin, wherein the biodegradable material of the first component, the second component, or both, is selected from the group consisting of polylactides, poly(lactic acid), polyglycolides, poly(glycolic acid), poly(trimethylene carbonate), poly(dioxanone), poly(hydroxybutyric acid), poly(hydroxyvaleric acid), poly(lactic-co-glycolic acid), poly(lactide-co-(epsilon-caprolactone-)), poly(glycolide-co-(epsilon-caprolactone)), polycarbonates, poly(pseudo amino acids), poly (amino acids), poly(hydroxyalkanoate)s, polyalkylene oxalates, polyoxaesters, polyanhydrides, polyester anyhydrides, polyortho esters, and copolymers, block copolymers, homopolymers, blends, and combinations thereof, and wherein the functional group of the first component is different than the functional group of the second component and the first component adheres to a tissue surface and the second component adheres to the implant.

U.S. Patent Publication No. 2006/0062768 titled Biocompatible hydrogel compositions, discloses a hydrogel composition for application to a tissue region of an animal comprising a first component comprising an electrophilic polymer material, and a second component comprising a nucleophilic material comprising autologous blood or an autologous blood component obtained from the animal that, when mixed in solution with the first component and applied to the tissue region, cross-links in situ with the first component to form a non-liquid structure.

U.S. Patent Publication No. 2003/0211137 titled Foam-forming wound dressing, discloses a foam wound dressing, comprising albumin and at least one additional protein.

U.S. Pat. No. 6,730,299 titled Adhesive protein foam for surgical and/or therapeutic uses, discloses a kit for preparing a biocompatible fluid adhesive protein foam, which is bioresorbable and nontoxic, for surgical and/or therapeutic use, in particular for protecting/cicatrizing tissue wounds and attaching biological tissues to each other or an implanted biomaterial, said kit comprising: a potentially adhesive protein compound which can be polymerized/crosslinked, solubilized in aqueous medium, in a first container; a polymerization/crosslinking agent for forming a biocompatible fluid adhesive protein matrix, which is bioresorbable and nontoxic, in a second container; a biocompatible and non-toxic gas or mixture of gases, either in the first, second and/or a third container; optional means for extemporaneously mixing the constituents, protein compound in aqueous solution and polymerization/crosslinking agent for forming the adhesive matrix, and, said gas or mixture of gases; whereby the protein foam is obtained in a ready to use form.

U.S. Pat. No. 5,840,777 titled Method of producing polysaccharide foams, discloses a method of forming a dry polysaccharide foam from an aqueous polysaccharide solution comprised of the steps of: a) forming an aqueous solution of a polysaccharide selected from the group consisting of alginic acid, a soluble alginate salt, and other soluble polysaccharides containing exchangeable counter-cations; b) introducing a gas into the aqueous solution to form a wet foam by agitating the solution; c) homogeneously dispersing an insoluble carbonate or hydrogen carbonate salt having one or more di- or tri-valent cations in the wet foam and subsequently treating the wet foam with an acid having a concentration not in excess of 1N thereby liberating carbon dioxide as a gas and the cations to produce a cross-linked polysaccharide foam; and d) drying the wet foam to form a dry polysaccharide foam; wherein the dry foam is predominantly comprised of polysaccharide.

U.S. Patent Publication No. 2002/0192271 titled Method for causing local hemostasis and hemostatic composition for local hemostasis, discloses a method for inducing hemostasis at a bleeding wound comprising providing topically to the site of the bleeding wound a hemostatically effective amount of FVIIa which is unaccompanied by other blood clotting factors and which has sufficient activity alone to produce a hemostatic effect, together with a biologically compatible carrier which permits said factor VIIa to remain in contact with said bleeding wound.

U.S. Patent Publication No. 2009/0287313 titled TISSUE ADHESIVE SEALANT, discloses a reinforced body tissue comprising a tissue adhesive sealant comprising: a cross-linkable protein; and a cross-linking agent solution comprising an aldehyde and an amino acid containing species reactive with said aldehyde, said aldehyde and said amino acid containing species being present in a ratio between 20:1 and 1:1 and said protein and said cross-linking agent are present in a ratio of between 15:1 and 1:1; in simultaneous contact with the body tissue and a patch.

U.S. Pat. No. 8,668,899 titled Advanced functional biocompatible foam used as a hemostatic agent for compressible and non-compressible acute wounds, discloses an apparatus for the treatment of wounds, comprising: a valve system attached to a canister containing a hydrophobically modified chitosan in a concentration of about 0.1% to about 2.0% by weight, wherein the hydrophobic modification of the chitosan is of 1 to 100 moles of a hydrophobic substituent per 1 mole of chitosan, and a propellant, wherein the hydrophobic modifications comprise hydrocarbon substituents of eight to twenty carbon residues in length covalently attached to chitosan.

PCT Patent Publication No. WO 2009/153748 Methods and devices for use with sealants, discloses use of a biocompatible medical adherent composition in a biological system, the composition comprising a non-fibrin cross-linkable polymer and an enzyme which induces cross-linking of said cross-linkable polymer, for thereby adhering at least a portion of the biological tissue, for reinforcement of surgical repair lines.

U.S. Pat. RE39321, titled Supplemented and unsupplemented tissue sealants, methods of their production and use, discloses an expanding fibrin sealant foam for treating wounded tissue in a patient comprising (i) fibrinogen, or a derivative or metabolite thereof, in an amount which forms a fibrin matrix; and (ii) an agent which causes fibrinogen to foam during application of said fibrinogen to wounded tissue, such that said fibrinogen expands to fill the wound and form a fibrin matrix that covers and adheres to said wounded tissue.

U.S. Pat. No. 5,874,500 titled Crosslinked polymer compositions and methods for their use, discloses a composition comprising a multi-nucleophilic polyalkylene oxide and a multi-electrophilic polyalkylene oxide, wherein the multi-nucleophilic polyalkylene oxide has m nucleophilic groups and the multi-electrophilic polyalkylene oxide has n electrophilic groups, wherein m and n are each greater than or equal to two, and wherein m+n is greater than or equal to five.

U.S. Pat. No. 6,258,351 titled Delivery of poly(ethylene glycol)-modified molecules from degradable hydrogels, discloses a degradable crosslinked polymeric structure comprising hydrolytically unstable linkages between one or more chemically crosslinked nonpeptidic polymers and conjugates of said nonpeptidic polymers and one or more bioactive agents; wherein said nonpeptidic polymers are selected from the group consisting of poly(alkylene oxides), poly(oxyethylated polyols), poly(olefinic alcohols), poly (acrylomorpholine), and mixtures thereof; and wherein said hydrolytically unstable linkages degrade in aqueous solution to release conjugates of said bioactive agents and said nonpeptidic polymers.

U.S. Pat. No. 6,566,406 titled Biocompatible crosslinked polymers, discloses a method for preparing a biocompatible crosslinked polymer hydrogel, comprising: providing a biocompatible small molecule crosslinker with a molecular weight of 2000 or less, the crosslinker having n crosslinker functional groups, wherein n is two or more, and wherein the crosslinker functional groups are either electrophilic or nucleophilic; providing a synthetic biocompatible functional polymer with a molecular weight of at least about 7 times more than the crosslinker, the functional polymer having m functional polymer functional groups, wherein m is two or more and the sum of n and m functional polymer functional groups, wherein m is two or more and the sum of n and m is five or more, and wherein the functional polymer functional groups are nucleophilic if the crosslinker functional groups are electrophilic, and the functional polymer functional groups are electrophilic if the crosslinker functional groups are nucleophilic; and combining the crosslinker and functional polymer to react the crosslinker functional groups with the functional polymer functional groups to form a hydrogel for which the crosslinked polymer gel time is less than 60 seconds as measured by a gel time measurement.

U.S. Pat. No. 8,034,367 titled Tissue adhering compositions, discloses a method comprising: mixing a first component, a second component, and a buffer material, the first component comprising an electrophilic polymer material comprising poly(ethylene glycol) having a functionality of at least three, the second component comprising a nucleophilic material comprising a recombinantly produced protein at a concentration of about 25% or less that, when mixed with the first component, cross-links with the first component to form a non-liquid, three-dimensional barrier, and the buffer material comprises tris-hydroxymethylaminomethane, and applying the mixture to body tissue, wherein the mixture forms a mechanical barrier on the body tissue.

U.S. Pat. No. 8,383,144 titled Tissue adhering compositions, discloses a method comprising: mixing a first electrophilic polymer material comprising poly(ethylene glycol) having a functionality of greater than or equal to three and a second electrophilic polymer material comprising a linear polymer with a solution comprising recombinant serum albumin having a concentration of about 25% by weight or less and a buffer material comprising tris-hydroxymethyl-aminomethane, said buffer material being capable of providing a reaction pH range of between about 8 to about 10, and applying the mixture to a tissue region, wherein the first electrophilic polymer material and the second electrophilic polymer material crosslink with the recombinant serum albumin to form a mechanical barrier.

U.S. Pat. No. 8,198,365 titled Lung volume reduction therapy using crosslinked non-natural polymers, discloses a method for reducing lung volume in a patient, comprising the step of administering to a patient in need thereof a therapeutically effective amount of a hydrogel, wherein said hydrogel is prepared from a first non-natural polymer and a first cross-linker; said first non-natural polymer comprises a plurality of pendant first nucleophilic groups; said first cross-linker comprises at least two pendant first electrophilic groups; and said first non-natural polymer consists essentially of a plurality of subunits independently selected from the group.

U.S. Pat. No. 7,766,891 titled Lung device with sealing features, discloses a method of performing tissue treatment or diagnosis in a subject, comprising: inserting a device into the subject and toward a lung along an entry path; pre-applying a cross-linkable tissue sealant from a sealant delivery element of the device to a region disposed along an external surface of a parietal parenchyma, within a plural space, and/or along an interior surface of a visceral pleura of the lung of the subject; advancing the device, after pre-applying the sealant, along the entry path and through the pre-applied sealant to a target site within the lung of the subject; and performing treatment or diagnosis at the site.

U.S. Pat. No. 8,057,818 titled Methods of making expandable foam-like biomaterials, discloses a method of making a biopolymeric material having a cellular foam structure comprising: combining a proteinaceous pre-polymeric liquid material and a cross linker solution to produce a mixture, wherein the proteinaceous pre-polymeric liquid material comprises a water soluble or plasma protein; introducing or producing a gaseous blowing agent into the proteinaceous pre-polymeric liquid material or the mixture; and allowing the mixture to cross-link and solidify simultaneously with the introduction or production of the gaseous blowing agent to thereby form the biopolymeric material having a cellular foam structure.

U.S. Pat. No. 8,071,124 titled Methods of using expandable foam-like biomaterials, discloses a method of treating a tissue site comprising: applying to the tissue site a proteinaceous pre-polymeric liquid material and a cross linker solution; combining the proteinaceous pre-polymeric liquid material and the cross linker solution to produce a mixture; introducing or producing a gaseous blowing agent into the proteinaceous pre-polymeric liquid material or the mixture; and allowing the mixture to solidify at the tissue site to thereby form a biopolymeric material having a cellular foam structure, to treat the tissue site.

U.S. Pat. No. 7,597,882 titled Protein crosslinkers, crosslinking methods and applications thereof, discloses a low molecular weight precursor comprising: a biocompatible liquid crosslinker with a molecular weight of no more than about 2000 Daltons that comprises at least three activated acid functional groups that are strong electrophiles selected from the group consisting of succinimide, succinimide ester, N-hydroxysuccinimide ester and maleimide, wherein the crosslinker forms a melt at less than about 50° C., wherein the strong electrophiles are not reactable by a Michaels-type reaction.

U.S. Pat. No. RE38827 titled Adhesive sealant composition, discloses an adhesive composition consisting essentially of i) a first aqueous mixture of about 20-60 wt/vol % serum albumin in about 0.01-0.25 molar buffer at a pH in a range of about 8.0-11.0, ii) a second aqueous mixture of about 50-800 mg/ml of a crosslinking agent having a molecular weight in a range of about 1,000-15,000, wherein the crosslinking agent is of the formula G-LM-PEG-LM-G wherein—PEG—is a diradical fragment represented by the formula —O—(CH 2-CH2-O—)$_a$— where a is an integer from 20-300; wherein—LM—is a diradical fragment selected from the group consisting of a carbonate diradical of the formula, —C(O)—, a monoester diradical of the formula, —(CH 2)$_b$C(O)— where b is an integer from 1-5, a diester radical of the formula, —C(O)—(CH2)$_c$—C(O)— where c is an integer from 2-10 and where the aliphatic portion of the diradical may be saturated or unsaturated, a dicarbonate diradical of the formula —C(O)—O—(CH 2)$_d$—O—C(O)— where d is an integer from 2-10, and an oligomeric diradical represented by the formulas —R—C(O)—, —R—C(O)—(CH2)$_c$-C(O)—, or —R—C(O)—O—(CH2)$_d$-O—C(O)— where c is an integer from 2-10, d is an integer from 2-10, and R is a polymer or copolymer having 1-10 monomeric fragments selected from the group consisting of lactide, glycolide, trimethylene carbonate, caprolactone and p-dioxanone; and wherein -G is a leaving group selected from the group consisting of succinimidyl, maleimidyl, phthalimidyl, imidazolyl, nitrophenyl or tresyl, and wherein a combination of the first and second mixtures is initially liquid and then cures on the surface of tissue to give a flexible, substantive matrix which bonds to the tissue and has a burst strength greater than about 10 mmHg.

China Patent Publication No. CN105521521A titled Lung sealing medical gel, and preparing method and application thereof discloses a medical product of serum albumin, comprising the following components: (1), a first liquid component, the liquid component containing dissolved into pH range for the concentration of 6.0-10.0 buffer solution is 5%-45% of germ and albumin (w/v), (2), the second solid component, the solid component is electrophilic functional group containing the hydrophilic polymer, the hydrophilic polymer selected from polyethylene glycol, polyethylene glycol oxide or polyethylene alcohol ethylene; wherein the solid component and the liquid component in the first germ albumin and the mass ratio is 0.3-2.

U.S. Patent Publication 2009/0221496 titled NOVEL ANTITHROMBOTIC AGENT discloses a pharmaceutical composition comprising an albumin conjugated with polyethylene glycol.

Foams are generally understood to represent materials in which a gas, such as air, is finely dispersed in a liquid in a form that is stable over some time. The liquid is found in the form of thin films between the bubbles. The stability of such gas dispersions is affected by the surface tension of the liquid phase. The surface tension can be influenced (reduced) by the presence of surface-active agents in the fluid phase, which help to stabilize the films against collapse. These foams are generally referred to as closed pore foams, as there is no connection between the gas spaces of each individual bubble. If the liquid films are stabilized by other means, e.g. by chemical reactions that transform the liquid phase into a viscoelastic solid, then the formation of open pore foams is possible. The transformation of the liquid films into a viscoelastic solid material also serves to effectively stabilize the foams against rapid collapse.

It is an object of the present invention to provide improved sealant and/or hemostatic foams which can be safely expressed onto tissue and which are effective in sealing tissue from leaks, particularly lung tissue. In addition, it is important that such a foam sealant/hemostat does not present a risk of obstruction or compression of pressure sensitive organs or tissues due to excessive swelling. There is a need in improved sealant/hemostatic foams and materials which facilitate ease of application and rapid onset of hemostasis.

SUMMARY OF THE INVENTION

The present invention is directed to tissue sealant compositions comprising: a multi-arm polyalkylene oxide, preferably polyethylene glycol, having at least 3 electrophilic groups; albumin; a buffer; water; and entrained gas as bubbles; wherein concentration of albumin in a liquid component of the sealant is within range of 50-200 mg/ml; and wherein concentration of multi-arm polymer component in said liquid component of the sealant is within range of 25-100 mg/mL. In another aspect, the present invention is directed to a method of making the tissue sealant, comprising: mixing and foaming a composition comprising multi-arm PEG-SG, albumin, buffer, water, and gas. In yet another aspect, the present invention is directed to a method of treating a wound by applying the sealant materials described above onto and/or into the wound of a patient.

DETAILED DESCRIPTION

Figure 1:
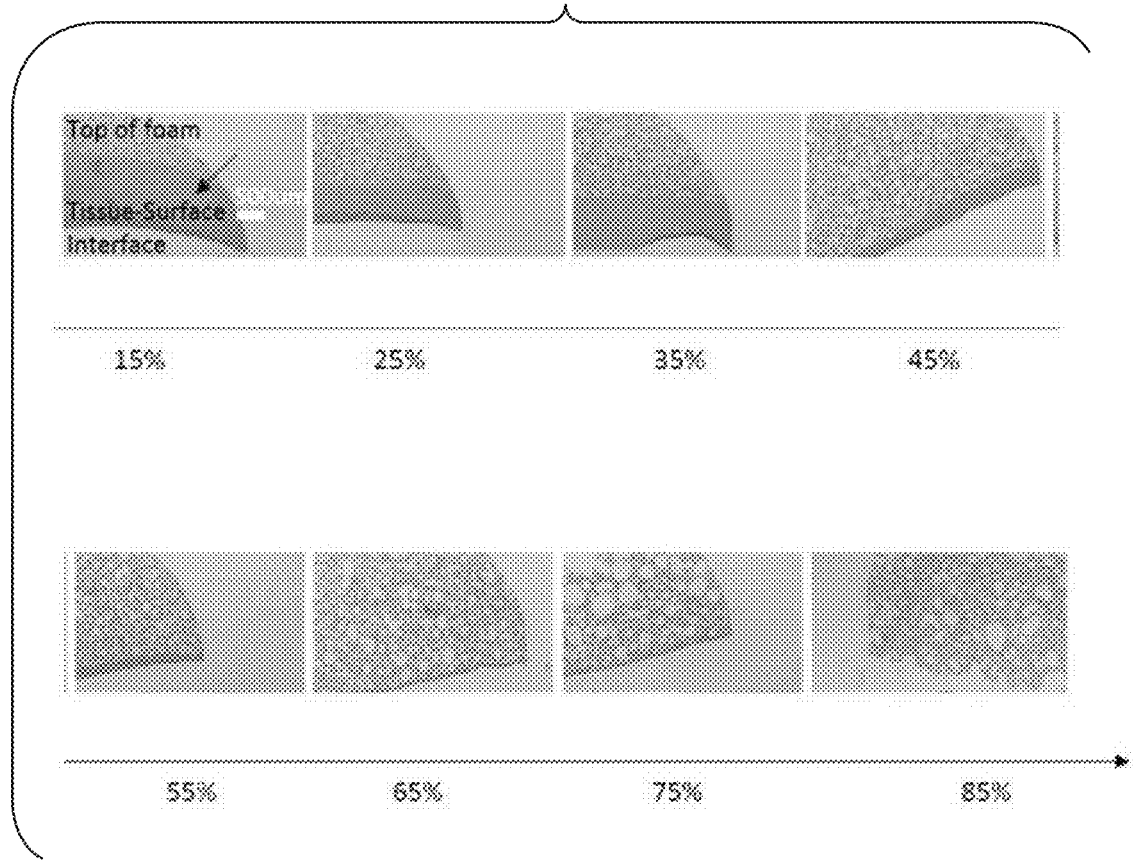
FIG. 1 shows micrographs of cross-sections of the cured foam presented for foams with variable air (% by volume) content.

The inventors have discovered sealing and hemostatic materials and process for making thereof, the sealant materials having surprising and highly beneficial properties for tissue sealing and hemostasis. More specifically, described are absorbable or bioresorbable tissue sealants comprising a polymerizable or curable foam comprising multi-arm PEG-NHS (where NHS is N-hydroxysuccinimide) (or PEG-SG, where SG is a succinimidyl glutarate ester), water, albumin, buffer, and gas, with the foam being able to seal lung air leaks, does not limit lung expansion, has acceptable runniness or viscosity. The gas component preferably comprises 55% to 75% of the foam by volume. The albumin/PEG-SG content is preferably defined by a) equation b) contour plot as will be shown below. The E modulus of the cured foam is preferably above 8.5 kPa and below 110 kPa. The multi-arm PEG-SG is also referred to as 2, 3, 4, 6,8 arm polyethylene glycol succinimidyl glutarate ester; PEG-SG4, PEG-SG2, 4-PEG-SG, PEG-SG 4-ARM, PEG-NHS, Succinimidyl PEG NHS, PEG-SUCCINIMIDYL GLUTARATE ESTER, tetra functional poly (ethylene glycol) succinimidyl glutarate, Multiple Arm PEG Polymer, PEG succinate-NHS, PEG-N-hydroxysuccinimide.

According to one embodiment of the present invention, the inventive composition comprises an absorbable compliant foam, comprising a) a protein, such as albumin; b) a polyethylene glycol (PEG) with at least 2 functionalized groups that can form a covalent bond with protein, such as NHS group; c) a gas which is used to form the foam and is present as bubbles trapped or encapsulated in the foam, with the gas component preferably comprises 55% to 75% of the foam volume; d) a fluid, such as water or saline; and e) an optional buffer which regulates pH. The foam is formed by mixing the above components and is applied to the tissue whereby the foam cures or cross-links while simultaneously bonding to the tissue. The foam is preferably characterized as compliant soft set foam with closed cell, a pliable liquid foam that is flowable, spreadable and/or a compliant soft set foam with closed cell.

The preferred tissue application of the foam is lung tissue, i.e. when the foam is brought into contact with several types of tissue, at least one of these is preferably lung tissue. The foam, even after curing needs to have good adhesion to tissue and simultaneously good compliance and compressibility to accommodate expansion and contraction of the lung. The present sealant can be applied to any tissue in vivo.

The inventive foam is a flowable foam that rapidly polymerizes (within a few minutes such as within interval from 0.5 min to about 30 min, more preferably 1 minutes-15 minutes, most preferably 1 minute to 10 minutes) to a soft or compliance and pliable cured or set foam.

In some embodiments, the inventive foams are prepared as a mixture of three components, 2 liquid components and gas or air. The liquid components can preferably include 2, 3, 4, 6, 8, etc. arm polyethylene glycol succinimidyl glutarate, such as 4-arm polyethylene glycol succinimidyl glutarate (PEG-SG4) and albumin dissolved in a buffered carbonate solution. Other aqueous solutions and solvents can be utilized as well. Albumin can be of any source, including animal derived, e.g. bovine, porcine, human derived, recombinant, etc.

One formulation embodiment includes 1 part liquid components (50 mg/ml PEG-SG4 in carbonate buffer and 100 mg/ml albumin in water) and 2 parts air or gas. To create an efficacious foam, ie, foam capable of sealing an air leak in the lung in an animal, the two liquid components and gas/air are combined and processed by passive or active techniques to generate a homogenous foam. Passive refers to methods such as passing components through beads, meshes, small orifices, while active methods require energy and include propellers and agitators. Upon mixing of the components, polymerization is initiated and by 30 seconds visual evidence of foam solidification occurs. Preferably, within about 2 minutes, the foam polymerization has progressed enough to seal an air leak in a preclinical air leak model.

Advantageously, the inventive foams have several benefits as flowable polymerizable soft set foams, including strong adherence with ability to stretch; conformability; targeted controlled application without runoff; ability to get into holes and fissures; visual confirmation of application without additives; greater coverage with less material, due to large volume to mass ratio limiting the amount of implanted material; ability to occupy space and bridge surfaces.

Example 1. Foams Preparation

Compliant foams comprising albumin at a concentration of 100 mg/ml of the liquid and 50 mg/ml of PEG-SG-4 having molecular weight of 10 kDa and varying volumes of air (0%, 15%, 25%, 35%, 45%, 55%, 65%, 75%, 85% of total foam volume) were prepared by a syringe exchange method as described below. The starting albumin concentration of the standard foam is 200 mg/ml, but after combining with the PEG-SG-4 in carbonate buffer, the final concentration of albumin is 100 mg/ml.

In one series of tests, the following materials were used: 200 mg/ml albumin (bovine serum albumin, Sigma) solution; PEG-SG-4 (Jenkem, China.) having molecular weight of 10 kDa; Buffer Carbonate at 100 mM concentration at pH 8; and Air—variable amounts as noted above and described below.

PEG-SG-4 powder was dissolved in 100 mM carbonate buffer (pH=8.0) to form 100 mg/mL solution. Albumin was dissolved in water to form 20% solution (w/v). 1.25 mL of 20% albumin solution and 1.25 mL of 100 mg/mL PEG-SG-4 in buffer were aspirated into separate 20 mL syringes. The volume of each syringe was adjusted to yield air content in the foams between 0% to 85% (air volume/total volume). The syringes were connected using a female-to-female or luer connector. The solutions were then rapidly passed back and forth or moved from one syringe to another and back for 20 times to create foams, with such mixing foaming performed over about 10-30 seconds. Such movement resulted in thorough mixing and formation of air-filled foam within the syringes. After forming the foam, the foam was finally transferred into the first syringe, the second syringe disconnected, and the foam expressed from the first syringe onto a substrate or onto a tissue for further evaluation and characterization.

The resulting foams were assessed for their physical attributes using quantitative methods as described below.

Example 2. Air Bubbles Distribution (at the Tissue-Foam Interface)

For the foam to be an effective lung sealant, the presence of air bubbles at the tissue-foam interface is important as it accommodates the change in lung surface and volume during lung inflation and deflation. Minimizing phase separation between the air and liquid is desirable. Foams with various air content (15% to 85% air volume/total volume) were made as described above and deposited on a horizontal flat polymeric surface and allowed to cure at least 10 minutes at room temperature 20-25 C. Once cured, the foams were processed in paraffin using standard histological techniques, sectioned and stained with hematoxylin and eosin (H&E). Referring to FIG. 1, micrographs of cross-sections of the cured foam are presented for foams with variable air (% by volume) content. Representative images of foams including the liquid or non-foamed phase as a function of air content are shown with the arrow indicating the liquid phase. The liquid phase refers to a portion of the expressed material that was non-foamed during or immediately collapsed after application. The liquid phase then cured and solidified as well as the foamed portion of the material.

As can be seen in FIG. 1, H&E stained cross-section images show a liquid phase having no air bubbles but only cured sealant at the interface between the foam sealant and the surface (bottom of foam, or lower area of the micrographs) representing collapsed foam. Such collapsed foam having no air bubbles can be seen to be significantly reduced as the air content in the foam increased, with very little liquid phase, if any as indicated by FIG. 1 at 45%-85%, and practically none at 65%-85%.

Figure 2:
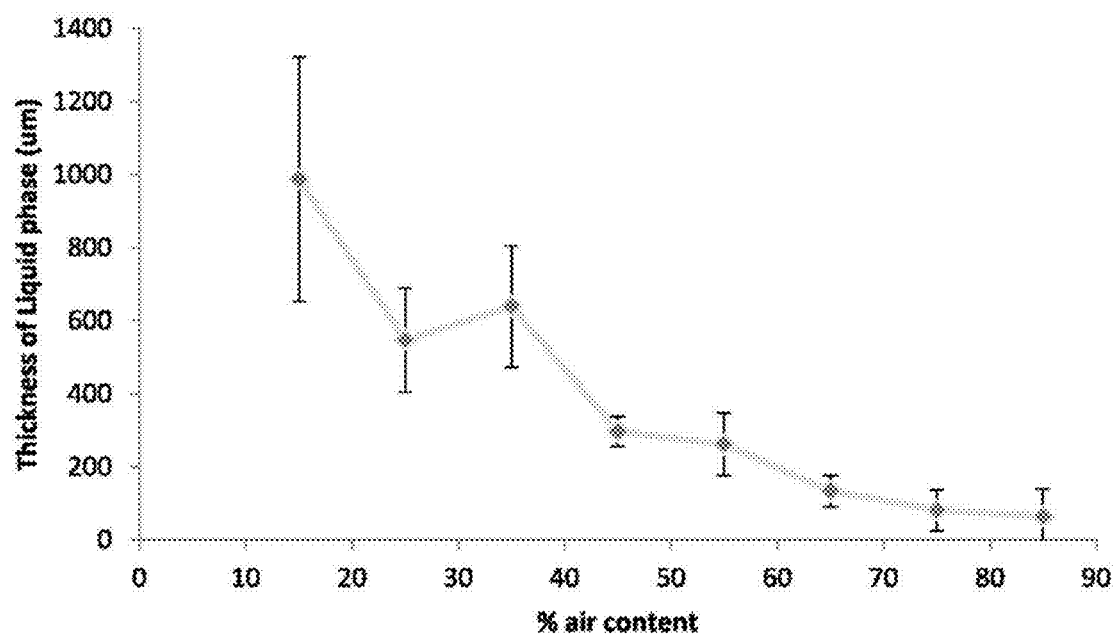
FIG. 2 shows chart of the thickness of the liquid phase layer vs. % air content in foam and analysis of phase separation or liquid phase thickness.

Analysis of phase separation or liquid phase thickness was performed in four cross-sections per foam and the results are shown in FIG. 2 as chart of the thickness of the liquid phase layer vs. % air content in foam. The results indicate that in 15% to 35% air content foams, relatively high thickness of liquid phase was present. In foams with 45% air content and above the liquid phase thickness are not statistically different to the negligibly low value observed for 85% air content foams (a thickness mean of 65 μm for 85% versus a thickness mean of 640 μm for 35%. ANOVA (analysis of variation) is a statistical test used to determine if there are statistically significant differences between the mean values of any groups in the study. Based on this evaluation, ~45% air content and above in the foam is preferred.

Example 3. Foam Flowability

For the foam to be useful in a lung sealant application, it is desirable to have a sealant that coats the tissue surface without running off while undergoing curing or cross-linking or polymerization. Low viscosity sealant will not stay in place long enough to cure and will migrate due to gravitational and other forces present. Foams made with the variable air content as described above were also prepared with similar compositions but having non-reactive PEG components (i.e. PEG with the same molecular weight but having no reactive SG or NHS groups). Such non-curing formulations were evaluated in order to eliminate the curing aspect of the foam for the flowability analysis. The viscosity and flowability of these non-curing foam formulations is expected to closely mimic these of the inventive curing formulations.

The non-curing foams were prepared using the syringe exchange method as explained in Example 1, but using non-reactive PEG. After forming the foam, 2 mL of the foam was dispensed vertically over the course of two seconds on a glass plate on an inclined plane set at 30 degrees. 30 degrees is the angle between the horizontal plane and the surface. The timer was started at the beginning of the dispense and the time at which the foam traveled 6 inches was recorded. Each group was tested twice from each preparation using two separate preparations for a total of n=4 samples. The flowability of the foams was thus measured as time required for the bead of foam to travel 6 inches on the inclined surface. Flowability is measured by applying the foam to an incline plane and measuring how long it takes (in seconds) to travel 6 inches. A foam that is not too runny is preferred so that is stays at the application site. It is preferred that foam takes longer than 7 seconds to travel the 6 inches on the incline plane.

Figure 3:
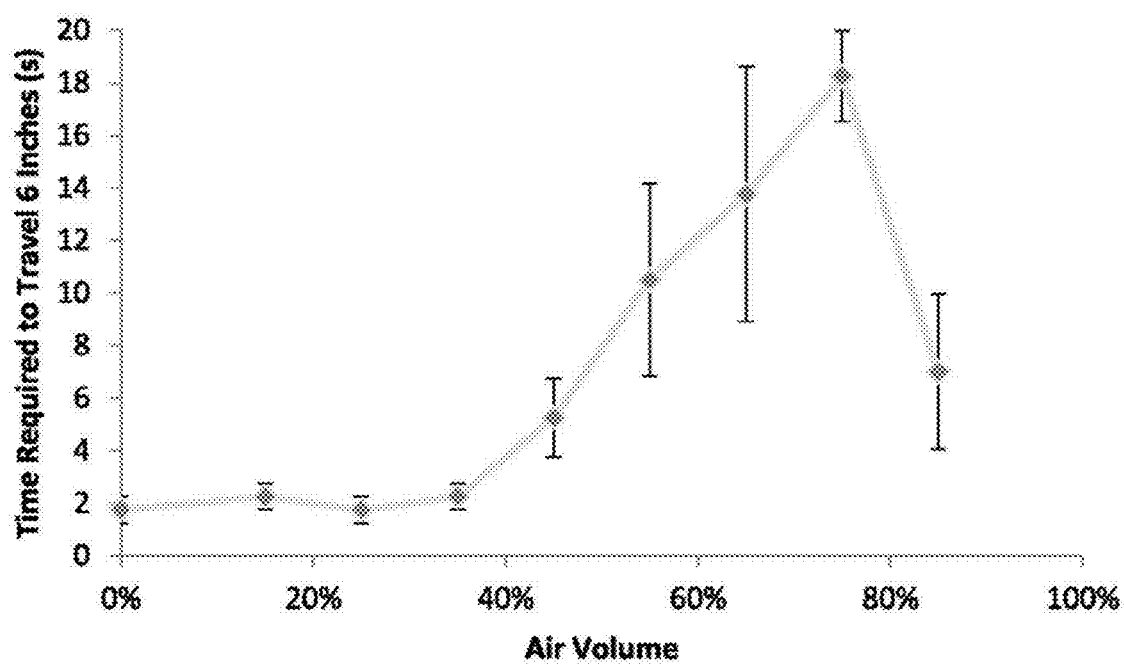
FIG. 3 shows results of foam flowability test as time (in seconds) to travel 6 inches vs. the air content of the foams.

Referring now to FIG. 3, the results of the flowability test are presented as the plot of the time (in seconds) to travel 6 inches vs. the air content of the foams.

As seen in FIG. 3, the travel time did not significantly increase from 0% to 45% air (p=0, one-way ANOVA). Advantageously, between 55% and 75% there was a significant increase in travel time compared with lower air content foams reflecting an optimal flowability of the foams, ie, a foam that will not migrate from the application site. 65% and 75% air content foams were statistically equivalent and were the least runny foams tested. There is a sharp increase in foam flowability when air content is increased from 75% to 85% resulting in the 85% air foam being statistically equivalent to the flowability observed for foams made with air content ranging between 0% and 45%. Therefore, in terms of foam flowability, the air content preferred range is between 55% and 75%, most preferred 65%-75% (air content/total foam volume). Bars show standard deviation.

The results demonstrate that the preferred air content in the inventive foams is in the range of 55% to 75% air content (air volume/total volume) as at these compositions the flowability is lowest, resulting in longest travel times which are above about 10 seconds or longer.

Based on the studied attributes of the inventive foams, specifically the air bubbles distribution and the flowability, the preferred range for air content in the inventive foams (% volume in total foam volume) is 55% to 75%.

Example 4. Foam Strength and Compliance

The inventors have further discovered specific advantageous properties of the inventive foams achieved at specific concentration ranges. Compliant foams were developed, the foams comprising albumin, polyethylene glycol (PEG) such as linear PEG or multi-arm (dendrimer) PEG with 4 arms or 8 arms or similar, with at least two or more functional groups (such as SG or NHS) that can form a covalent bond with proteins; gas such as air; and optional buffer. PEG-SG and protein concentrations are defined by an experimentally derived regression equation of "E modulus (kPa)", where the concentrations yield optimal E modulus (kPa) value that is above 8.5 kPa and below 110 kpa.

Compliant foams were prepared, comprising 66% of air (% volume); variable concentration of albumin (ranging between 50 and 200 mg/ml of the liquid portion of the foam); and variable concentration of PEG-SG4-10K (ranging between 25 and 100 mg/ml of the liquid portion).

The compositions were prepared as described above and foamed by syringe exchange method. The foams were allowed to cure inside a fixture having a hollow cylindrical opening (height of 18.5 mm and cross sectional surface area of 194.8 mm^2) for 10 minutes. The cured foams inside the cylindrical opening were then characterized for their biomechanical integrity by measuring the foam's elasticity under cyclical normal to surface mechanical load and record the E modulus (kPa) using an Instron electromechanical testing apparatus.

The compositions of the tested foams and the E modulus are shown in Table 1.

TABLE 1

Foam E modulus as a function of PEG-SG4-10K and Albumin concentrations.

| PEG-SG4-10K (mg/ml) | Protein (Albumin mg/ml) | E (kPa) |
|---|---|---|
| 25 | 50 | 3.09 |
| 25 | 50 | 3.80 |
| 50 | 100 | 19.23 |

TABLE 1-continued

Foam E modulus as a function of PEG-SG4-10K and Albumin concentrations.

| PEG-SG4-10K (mg/ml) | Protein (Albumin mg/ml) | E (kPa) |
|---|---|---|
| 50 | 100 | 21.61 |
| 50 | 100 | 25.64 |
| 100 | 200 | 116.34 |
| 100 | 50 | 6.89 |
| 100 | 50 | 6.65 |
| 100 | 50 | 6.17 |
| 25 | 200 | 18.52 |
| 25 | 200 | 18.76 |
| 50 | 200 | 73.13 |
| 50 | 200 | 61.97 |
| 25 | 100 | 10.68 |
| 25 | 100 | 9.26 |
| 25 | 100 | 10.68 |
| 100 | 100 | 36.09 |
| 100 | 100 | 46.53 |
| 50 | 50 | 5.70 |
| 50 | 50 | 5.70 |
| 50 | 50 | 11.40 |

Figure 4:
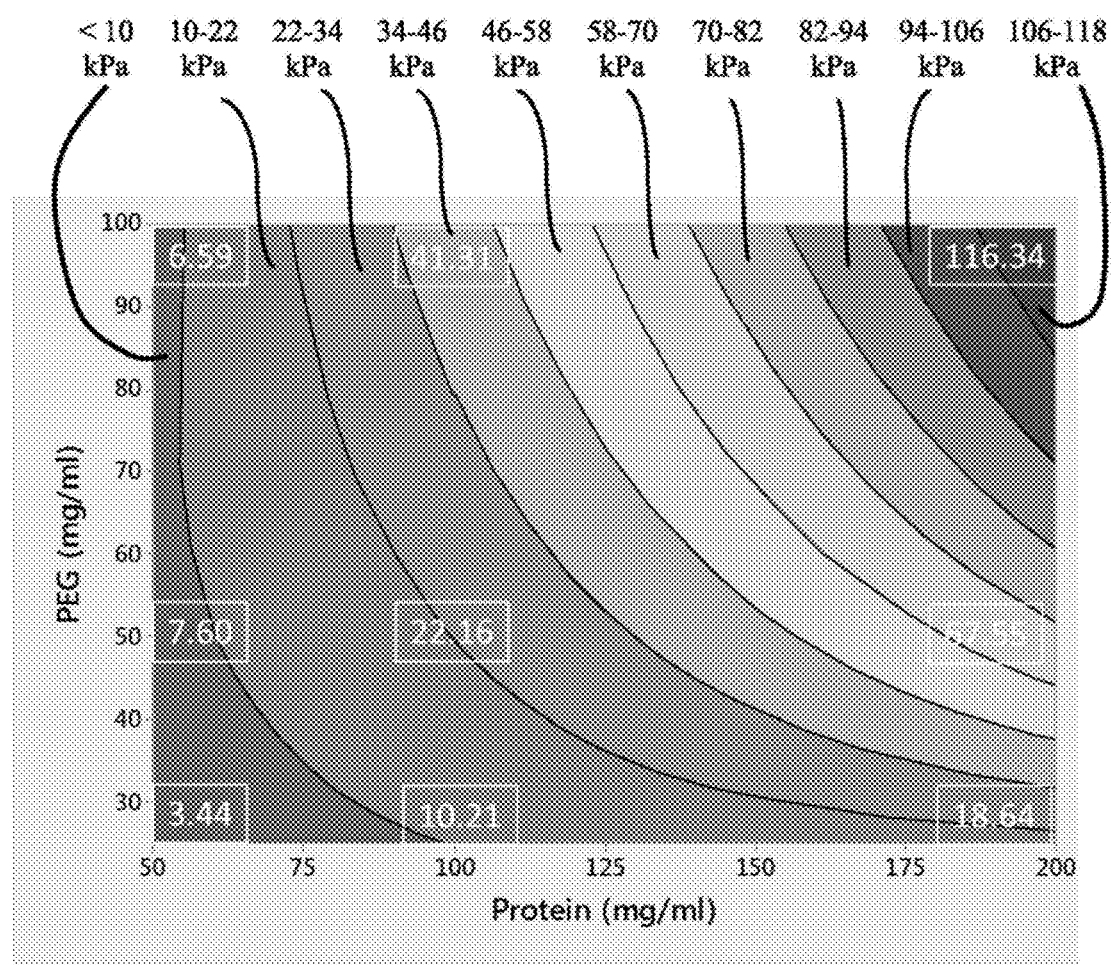
FIG. 4 shows contour plot of foam elasticity (E modulus; kPa) vs. PEG (mg/ml) and albumin (protein) (mg/ml).

The experimental data in Table 1 was processed using Minitab statistical (version 17) to yield the contour plot shown in FIG. 4. FIG. 4 shows a contour plot of foam elasticity (E modulus; kPa) vs. PEG (mg/ml) and albumin (protein) (mg/ml). The ranges for each band of the contour plot are shown as well. The average value for each of the 9 recorded concentration combinations are indicated on the plot outlined in squares. The concentration scale presented in FIG. 4 does not start at the value of zero. Foams made with PEG concentration below 25 mg/ml and albumin concentration below 50 mg/ml in the liquid portion of the foam yielded poor foam biomechanical integrity and therefore, were not further evaluated.

Example 5. Testing of Critical Biomechanical Requirements for the Foam in Terms of E Modulus The critical biomechanical requirements for the foam in terms of E modulus (kPa) were determined based on ex-vivo studies where various concentrations from Table 1 were tested on ventilated/expanding lung tissue and the feasibility of the foam as a sealant was scored by the pre-clinical surgeon as acceptable or not-acceptable.

The foams were prepared by the dual syringe exchange method using 2.5 mL of solution of the specific concentration of PEG-SG4-10K, 2.5 mL of solution of the specific concentration of albumin and 10 mL of air. The components were rapidly passed 20 times between syringes to achieve a homogenous foam, which was immediately applied to the lung tissue.

Figure 5:
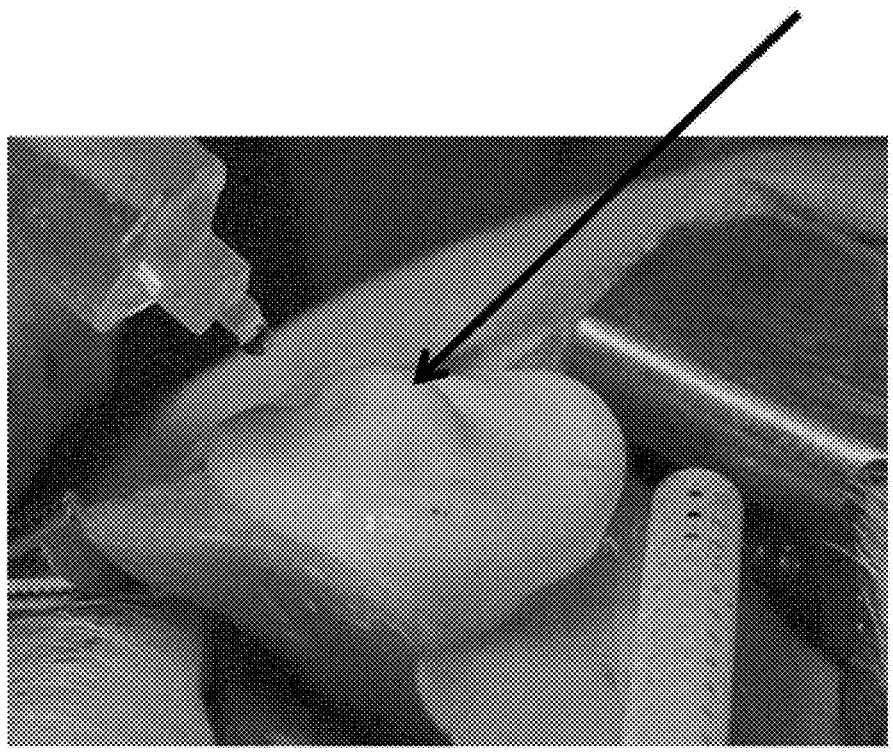
FIG. 5 shows testing of foam in a lung ex-vivo defect model.

Example of failure at the lower end of the E modulus range. Foam made by a syringe exchange method with 66% air content (air volume/total volume) and with 25 mg/ml of PEG-SG-4-10K and 50 mg/ml albumin in the liquid portion of the foam, which exhibited E modulus of ~3 kPa was applied to a ventilated cadaver porcine lung ex-vivo model. After being applied to lung tissue, this foam demonstrated a mechanical failure as shown in FIG. 5, due to low mechanical integrity, and was scored as un-acceptable to be used as a sealant by the surgeon. FIG. 5 shows testing of foam in a cadaver porcine lung ex-vivo defect model. Arrow indicates the foam failure location as evidenced by the bulging of the foam over the defect due to air pressure from the lung. As a consequence of the reduced concentrations of albumin and PEG crosslinker, the foam's low biomechanical integrity shows inability to serve as a sealant barrier during ventilations due to a pocket of air formed over the defect under the foam.

Figure 6A:
FIGS. 6A-B show rigidity and poor compliance of high modulus foams applied
Figure 6B:

Example of failure at the higher end of the E modulus range. Conversely, foam made with 100 mg/ml of PEG-SG-4-10K and 200 mg/ml albumin in liquid portion of the foam, which exhibited E modulus of ~116 kPa was tested and found to be too rigid and thus was restricting lung expansion as indicated by the deformation of the lung tissue as it expands. After being applied to lung tissue, this foam demonstrated unacceptable rigidity and lack of compliance as shown in FIG. 6. FIG. 6A shows the high modulus foam applied to deflated porcine lung surface in an ex-vivo model. The lung maintains physiological structure. FIG. 6B shows that once the same lung is ventilated and expands, the areas in proximity to the high modulus foam deform into an unnatural, non-physiological shape and it appears that the natural expansion of the lung is constricted by the high E modulus foam. This phenomenon was not observed in lower E modulus foams tested. The performance of the high E modulus foam was deemed unacceptable.

The high E modulus foam was prepared by the dual syringe exchange method using 2.5 mL of 200 mg/mL PEG-SG4-10K, 2.5 mL of 40% albumin and 10 mL of air. The concentrations represent the starting concentrations of the components before mixing in a 1:1 ratio. After the mixing of albumin and PEG, the concentrations are 50% lower.

Example of successful performance in the middle range of the E modulus range. Foams prepared with amounts of PEG crosslinker and albumin within the optimal sealing range were tested in the same model (foam made with 50 mg/ml of PEG-SG-4-10K and 100 mg/ml albumin in liquid portion of the foam having a 1:2 liquid to air ratio). We have tested the optimal foam in the ex vivo model and it adhered well and complied with the lung during ventilations. The foam did not delaminate i.e. did not separate from the tissue, and the foam maintained its cohesive properties, i.e. the foam did not crack or rupture.

Figure 7A:
FIGS. 7A-D show application of the foam sealant to an air leak defect model and testing of the performance.
Figure 7B:
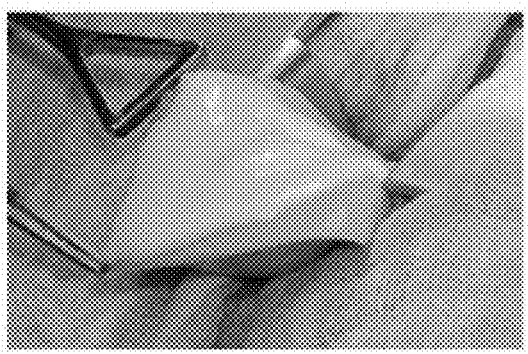
Figure 7C:
Figure 7D:
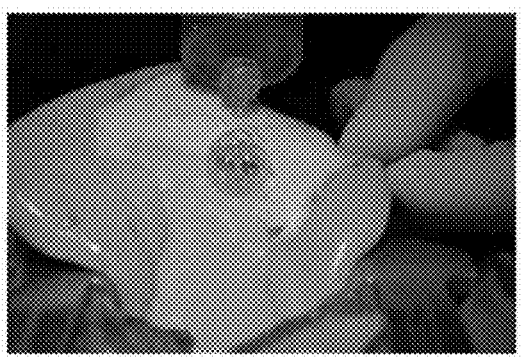

Example of successful performance in the middle range of the E modulus range. Foam prepared with amounts of PEG crosslinker and albumin within the optimal sealing range were shown to seal air leaks in the ex-vivo model above as well as in a canine prolonged air leak model in acute and survival pre-clinical studies. The foam formulation used consisted of 50 mg/ml PEG-SG4 and 100 mg/ml albumin. Referring to FIG. 7, the data indicates that the foam sealant can successfully seal an air leak in the canine model. FIG. 7A shows application of the foam sealant to an air leak defect model. When the foam was applied, it flowed over the surface and coated the defect. After 2 minutes, the foam polymerized to form an adhesive and cohesive barrier that sealed the air leak (FIG. 7B). The leak was tested by a bubble leak test at 20 cm water pressure in the lung to ensure the leak was sealed (FIG. 7C). After confirmation of the sealed leak, the foam was peeled away to demonstrate that the leak had not spontaneously resolved and therefore scored as acceptable by the surgeon (FIG. 7D showing air leak still present after foam removal). This indicates that a foam with a biomechanical integrity of ~22 kPa provided was rigid but also pliable/complaint enough to prevent air leak without constricting the lung natural expansion.

Referring to Table 2, comparison of different foams and their properties is presented. The foams with low E modulus (3.44) are compared to foams with intermediate E modulus (22.16) and to foams with high E modulus (116.34). It can be seen that only foams with an intermediate E modulus are able to meet all criteria, including sealing air leaks, not limiting lung expansion, and having acceptable runniness.

TABLE 2

Comparison of different formulations of foams and their properties

| Criteria | Formulations | | |
|---|---|---|---|
| | 25 mg/ml of PEG-SG-4-10K and 50 mg/ml albumin | 50 mg/ml of PEG-SG-4-10K and 100 mg/ml albumin | 100 mg/ml of PEG-SG-4-10K and 200 mg/ml albumin |
| E modulus (kPa) | 3.44 | 22.16 | 116.34 |
| Sealing air leaks | No | Yes | Yes |
| Does not limit lung expansion | Yes | Yes | No |
| Acceptable Runniness | No | Yes | No |

A regression model was developed based on the experimental data to represent the relationship between foam biomechanical properties and the PEG and albumin concentrations. Regression Analysis was performed for E Modulus (kPa) versus Albumin, PEG concentrations and the results are shown in Tables 3-6.

TABLE 3

Analysis of Variance

| Source | DF | Adj SS | Adj MS | F-Value | P-Value |
|---|---|---|---|---|---|
| Regression | 5 | 15922.3 | 3184.46 | 136.19 | 0 |
| Albumin | 1 | 44.1 | 44.11 | 1.89 | 0.19 |
| PEG | 1 | 15 | 15 | 0.64 | 0.436 |
| Albumin*Albumin | 1 | 18.6 | 18.57 | 0.79 | 0.387 |
| PEG*PEG | 1 | 158.6 | 158.63 | 6.78 | 0.02 |
| Albumin*PEG | 1 | 3841.6 | 3841.63 | 164.29 | 0 |
| Error | 15 | 350.7 | 23.38 | | |
| Lack-of-Fit | 3 | 189.4 | 63.14 | 4.7 | 0.022 |
| Pure Error | 12 | 161.3 | 13.44 | | |
| Total | 20 | 16273.1 | | | |

TABLE 4

Model Summary

| S | R-sq | R-sq(adj) | R-sq(pred) |
|---|---|---|---|
| 4.83559 | 97.84% | 97.13% | 93.93% |

TABLE 5

Coefficients

| Term | Coef | SE Coef | T-Value | P-Value | VIF |
|---|---|---|---|---|---|
| Constant | −2.34 | 9.89 | −0.24 | 0.816 | |
| Albumin | −0.168 | 0.123 | −1.37 | 0.19 | 44.62 |
| PEG | 0.197 | 0.246 | 0.8 | 0.436 | 48.21 |
| Albumin*Albumin | 0.00039 | 0.00044 | 0.89 | 0.387 | 37.91 |
| PEG*PEG | −0.00462 | 0.00177 | −2.6 | 0.02 | 42.13 |
| Albumin*PEG | 0.00832 | 0.00065 | 12.82 | 0 | 6.9 |

$E$ Modulus $(kPa) = -2.34 - 0.168\,\text{Albumin} + 0.197\,PEG + 0.000393\,\text{Albumin}*\text{Albumin} - 0.00462\,PEG*PEG + 0.008318\,\text{Albumin}*PEG$ Regression Equation

TABLE 6

Fits and Diagnostics for Unusual Observations

| Obs | E Modulud (kPa) | Fit | Resid | Std Resid | |
|---|---|---|---|---|---|
| 6 | 73.13 | 61.21 | 11.92 | 2.9 | R |

R Large residual

Regression Equation Obtained (Inserting the Albumin and PEG Concentration in mg/ml) is as Follows:

$E$ Modulus $(kPa) = -2.34 - 0.168\,\text{Albumin} + 0.197\,PEG + 0.000393\,\text{Albumin}^2 - 0.00462\,PEG^2 + 0.008318\,\text{Albumin}*PEG$ Based on the regression model 95% confidence interval (IC) at the data points showed biomechanical integrity insufficiency, a range of "E modulus (kPa)" of above 8.5 kPa and below 110 kPa was determined to be critical to provide acceptable foam sealant performance.

Figure 8:
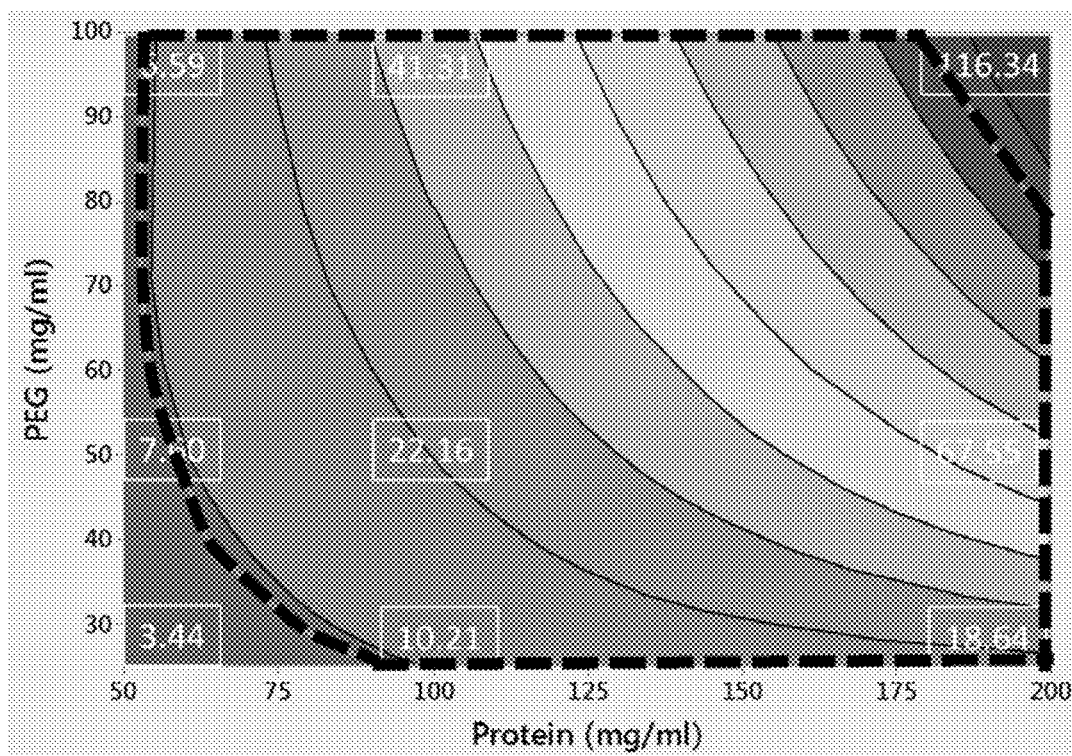
FIG. 8 shows the same contour plot of foam elasticity as shown in FIG. 4, but with the desirable concentrations space defined by the dotted line.

The PEG and albumin concentrations that define this critical "E modulus (kPa)" biomechanical desired range can be obtained by setting the "E modulus (kPa)" in the equation above to be above 8.5 kPa and below 110 kPa. This range is illustrated as the inner surface of the dashed, closed geometric shape in FIG. 8. FIG. 8 is the same contour plot of foam elasticity as shown in FIG. 4, but with the desirable concentrations space defined by the dotted line. The PEG and Albumin Concentrations that intersect within this shape are the preferred range of concentrations to be used in the foam. The surface inside the dashed, closed geometric shape represents the biomechanical acceptable region for foam sealants (Above 8.5 and below 110 kPa E modulus).

Example 6. Comparative Data for Non-Foam Liquid-Only Sealant

Figure 9:
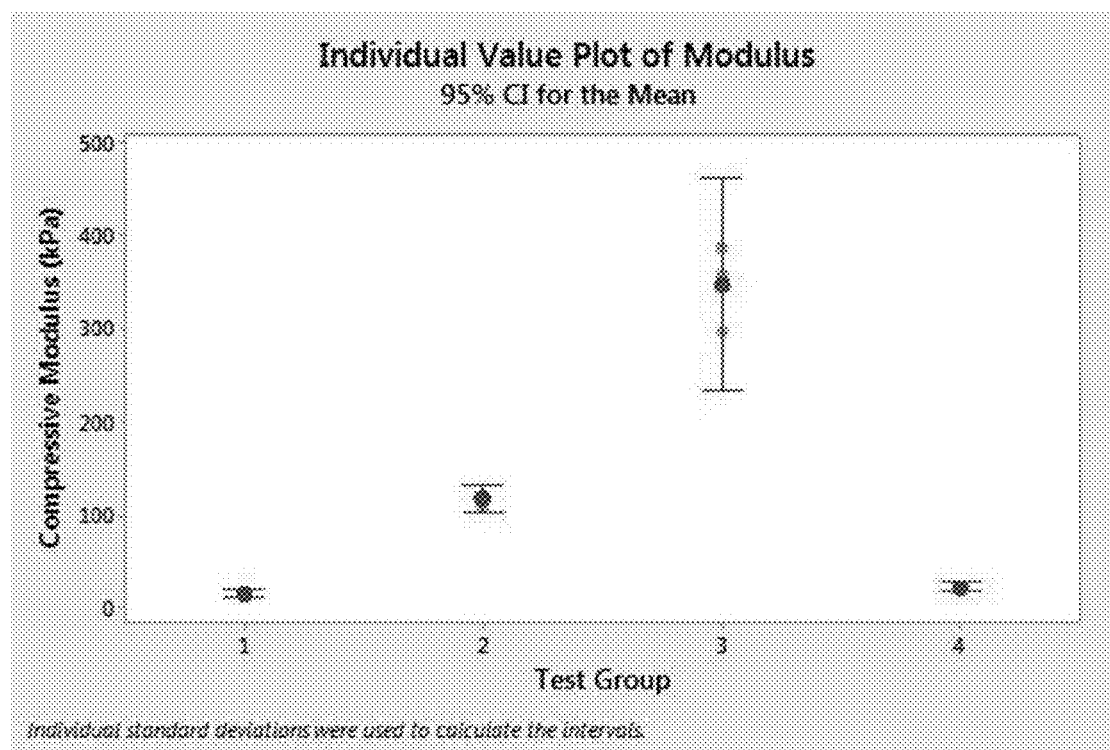
FIG. 9 shows the results of testing of 3 levels of albumin and PEG-SG4 concentration compositions in liquid sealant form, with foamed compositions also included as a control

Modulus data for comparing foamed and liquid-only compositions was obtained for the compression modulus. The liquid sealant formulations were tested at 3 levels in exactly the same way as in the foam testing, but using a liquid formulation instead (no air). The results of testing of 3 levels of albumin and PEG-SG4 concentration compositions in liquid sealant form, with foamed compositions also included as a control are presented in Table 7 and in FIG. 9. The results show that the "standard" concentration of liquid yielded results outside the preferred range identified for the foam (8.5-110 kPa modulus). The "standard" concentration of liquid represents the same concentration of albumin (100 mg/ml) and PEG-SG4 (50 mg/ml) as that found in the liquid portion of the foam having a 1:2 liquid to air ratio), which was found to be acceptable in the preclinical animal model. The foam performed similarly to the previously presented data and demonstrated advantageous properties as discussed above.

TABLE 7

Compressive Modulus comparisons for foamed and liquid-only sealants

| Formulation (Mixing Technique) | Compressive Modulus (kPa) Mean |
|---|---|
| Low Concentration Liquid (50 mg/mL albumin and 25 mg/mL PEG-SG4-10k, no air) Sealant Formulation | 15.89 |
| Standard Concentration Liquid (100 mg/mL | 118.00 |

TABLE 7-continued

Compressive Modulus comparisons for foamed and liquid-only sealants

| Formulation (Mixing Technique) | Compressive Modulus (kPa) Mean |
|---|---|
| albumin and 50 mg/mL PEG-SG4-10k, no air) Sealant Formulation | |
| High Concentration Liquid (200 mg/mL albumin and 100 mg/mL PEG-SG4-10k, no air) Sealant Formulation | 347.60 |
| Standard Titan Foam (100 mg/mL albumin and 50 mg/mL PEG-SG4-10k, 1:2 liquid to air ratio) | 22.57 |

Example 7. Methods of Making and Treating

According to embodiments of the present invention, there is provided a method of making a foam for lung sealing applications, comprising the steps of mixing the components and sequentially or simultaneously adding gas forming a foam, then immediately expressing the resulting foam onto lung tissue and allowing the foam to cure. The mixing and foaming steps are preferably performed rapidly, such as over 20 s-2 min, such as over 30 s-1 min. The mixing and foaming steps are performed so that no substantial curing can occur prior to expressing the foam onto tissue.

The mixing and foaming steps can be performed in a variety of sequences and some are illustrated below. The foaming step can be performed by injecting gas, high speed mixing with gas, co-expression through static mixers, and other methods of making foams known to a skilled artisan. Examples of mixing sequences include:

Foaming all-Component Mixture M3
Two Liquid Precursors Method of Making Steps:
Preparing a mixture M1 of reactive PEG and water and optional buffer;
Preparing a mixture M2 of albumin and water and optional buffer;
Rapidly intermixing M1 and M2 forming mixture M3;
Adding a gas and rapidly foaming M3;
Immediately thereafter expressing M3 onto lung tissue;
Allowing M3 to cure on tissue.
One Liquid Precursor with Peg Method of Making Steps:
Preparing a mixture M1 of reactive PEG and water and optional buffer;
Rapidly intermixing M1 and powdered albumin forming mixture M3;
Adding a gas and rapidly foaming M3;
Immediately thereafter expressing M3 onto lung tissue;
Allowing M3 to cure on tissue.
One Liquid Precursor with Albumin Method of Making Steps:
Preparing a mixture M2 of albumin and water and optional buffer;
Rapidly intermixing M2 and powdered reactive PEG forming mixture M3;
Adding a gas and rapidly foaming M3;
Immediately thereafter expressing M3 onto lung tissue;
Allowing M3 to cure on tissue.
Dry Mixture Precursor Method of Making Steps:
Preparing a dry mixture M4 of reactive PEG and albumin and optional buffer;
Rapidly intermixing M4 with water and optional buffer forming mixture M3;
Adding a gas and rapidly foaming M3;
Immediately thereafter expressing M3 onto lung tissue;
Allowing M3 to cure on tissue.
Pre-Foaming Intermediate Compositions M1 or M2
Two Liquid Precursors Method of Making Steps:
Preparing a mixture M1 of reactive PEG and water and optional buffer;
Adding a gas and rapidly foaming M1;
Preparing a mixture M2 of albumin and water and optional buffer;
Rapidly intermixing foamed M1 with M2 forming mixture M3;
Immediately thereafter expressing M3 onto lung tissue;
Allowing M3 to cure on tissue.
Or
Preparing a mixture M1 of reactive PEG and water and optional buffer;
Preparing a mixture M2 of albumin and water and optional buffer;
Adding a gas and rapidly foaming M2;
Rapidly intermixing foamed M2 with M1 forming mixture M3;
Immediately thereafter expressing M3 onto lung tissue;
Allowing M3 to cure on tissue.
One Liquid Precursor with Peg Method of Making Steps:
Preparing a mixture M1 of reactive PEG and water and optional buffer;
Adding a gas and rapidly foaming M1;
Rapidly intermixing foamed M1 and powdered albumin forming mixture M3;
Immediately thereafter expressing M3 onto lung tissue;
Allowing M3 to cure on tissue.
One Liquid Precursor with Albumin Method of Making Steps:
Preparing a mixture M2 of albumin and water and optional buffer;
Adding a gas and rapidly foaming M2;
Rapidly intermixing foamed M2 and powdered reactive PEG forming mixture M3;
Immediately thereafter expressing M3 onto lung tissue;
Allowing M3 to cure on tissue.

According to embodiments of the present invention, there is provided a method of treating a lung tissue by applying a compliant and curable foam prepared by the methods described above and comprising components described above. According to embodiments, a foam is prepared and immediately dispensed, prior to complete curing, more preferably prior to any substantial curing, such as prior to viscosity changing after mixing not more than 50%, such as not more than 40%, more preferably not more than 25%, such as not more than 10%, expressing the foam onto lung tissue and allowing the foam to cure.

A number of additives may be delivered with/in the foam sealant, including chemotherapeutic agents, growth factors, cytokines, antimicrobials, procoagulant hemostatic agents, antifibrinolytics, etc.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A tissue sealant comprising:
   a) a multi-arm PEG having at least 3 electrophilic groups;
   b) albumin;
   c) a buffer;
   d) water; and
   e) entrained gas as bubbles;
   wherein when components (a-e) of the tissue sealant are combined produce a compliant soft set foam with closed cell;
   wherein concentration of albumin in a liquid component of the sealant is within range of 50-200 mg/ml; and
   wherein concentration of multi-arm PEG in said liquid component of the sealant is within range of 25-100 mg/mL,
   wherein gas comprises 65% to 75% of the foam by volume, and
   wherein E modulus of the foam in a cured state is above 8.5 kPa and below 110 kPa.

2. The tissue sealant of claim 1, wherein said gas is air, nitrogen, argon, carbon dioxide, or mixtures thereof.

3. The tissue sealant of claim 1, wherein said multi-arm PEG has molecular weight from about 5 kD to about 20 kD.

4. The tissue sealant of claim 1, wherein said multi-arm PEG comprises diester linkages.

5. The tissue sealant of claim 1, wherein said electrophilic groups are hydroxysuccinimide (NHS) or succinimidyl glutarate ester (SG).

6. The tissue sealant of claim 1, wherein said sealant comprises a foam and is bioresorbable.

7. The tissue sealant of claim 6, wherein foam flowability is such that the foam requires at least 7 seconds to travel 6 inches on a 30% inclined panel.

8. The tissue sealant of claim 6, wherein albumin and PEG-SG concentrations in mg/mL of liquid portion of the foam, are selected so that an equation for E Modulus yields values from 8.5 kPa to 110 kPa:

$$E \text{ Modulus } (kPa) = -2.34 - 0.168 \text{Albumin} + 0.197 PEG + 0.000393 \text{Albumin}^2 - 0.00462 PEG^2 + 0.008318 \text{Albumin} * PEG.$$

9. A method of making the tissue sealant of claim 1, comprising: mixing and foaming a composition comprising multi-arm PEG-SG, albumin, buffer, water, and gas.

10. A method of using the tissue sealant of claim 1, comprising:
    rapidly mixing and foaming a composition comprising multi-arm PEG-SG, albumin, buffer, water, and gas, forming a foam;
    immediately thereafter applying the foam onto a tissue;
    allowing the foam to cure on said tissue.

* * * * *